US010463471B2

(12) United States Patent
Bouduban et al.

(10) Patent No.: US 10,463,471 B2
(45) Date of Patent: Nov. 5, 2019

(54) METHODS AND DEVICES FOR POSITIONING AND SECURING LIGAMENT GRAFTS

(71) Applicant: Medos International Sárl, Le Locle (CH)

(72) Inventors: Nicolas Bouduban, Bruegg (CH); Patrick Burki, Solothurn (CH); Philippe Gedet, Nidau (CH); Beat Lechmann, Grenchen (CH)

(73) Assignee: MEDOS INTERNATIONAL SARL, Le Locle (CH)

( * ) Notice: Subject to any disclaimer, the term of this patent is extended or adjusted under 35 U.S.C. 154(b) by 908 days.

(21) Appl. No.: 14/328,362

(22) Filed: Jul. 10, 2014

(65) Prior Publication Data

US 2015/0025631 A1 Jan. 22, 2015

Related U.S. Application Data

(60) Provisional application No. 61/847,900, filed on Jul. 18, 2013.

(51) Int. Cl.
*A61F 2/08* (2006.01)
*A61B 17/04* (2006.01)

(52) U.S. Cl.
CPC ........ *A61F 2/0811* (2013.01); *A61B 17/0401* (2013.01); *A61B 2017/0414* (2013.01);
(Continued)

(58) Field of Classification Search
CPC ............ A61F 2/0811; A61F 2002/0852; A61F 2002/0858; A61F 2002/0888; A61F 2002/0817; A61F /
See application file for complete search history.

(56) References Cited

U.S. PATENT DOCUMENTS 4,045,418 A    8/1977   Sinclair
4,057,537 A   11/1977   Sinclair
(Continued)

FOREIGN PATENT DOCUMENTS

EP      1332729 A1    8/2003
EP      1645247 A1    4/2006
(Continued)

OTHER PUBLICATIONS

Allcock. "Polyphosphazenes." *The Encyclopedia of Polymer Science.* New York: John Wiley & Sons. 13(1988):31-41.
(Continued)

*Primary Examiner* — Thomas Sweet

(57) ABSTRACT

Methods and devices for positioning and securing ligament grafts are provided. In general, the devices and methods utilize an implant having a particular outer surface profile and a bone tunnel having a complementary profile to provide a form fit between the implant and bone that utilizes friction to position and secure a ligament graft within the bone. Such an implant can be used in conjunction with a variety of ligament grafts, including hamstring ligament grafts. In addition, an "outside in" approach can be utilized with the implant to minimize the risk of damaging adjacent tissue during an operation and provide enhanced surgeon control. The devices and methods can be utilized in connection with repairing or replacing ligaments in a variety of joints, but can in some embodiments have particular utility in cruciate ligament reconstruction procedures.

17 Claims, 15 Drawing Sheets

(52) U.S. Cl.
CPC .............. *A61B 2017/0427* (2013.01); *A61F 2002/0852* (2013.01); *A61F 2002/0882* (2013.01); *A61F 2230/0067* (2013.01)

(56) References Cited

U.S. PATENT DOCUMENTS

| | | | |
|---|---|---|---|
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,205,399 A | 6/1980 | Shalaby et al. |
| 4,208,511 A | 6/1980 | Shalaby et al. |
| 4,927,421 A | 5/1990 | Goble et al. |
| 5,037,422 A | 8/1991 | Hayhurst et al. |
| 5,100,417 A | 3/1992 | Cerier et al. |
| 5,176,682 A | 1/1993 | Chow |
| 5,224,946 A | 7/1993 | Hayhurst et al. |
| 5,236,445 A | 8/1993 | Hayhurst et al. |
| 5,258,016 A | 11/1993 | DiPoto et al. |
| 5,354,298 A | 10/1994 | Lee et al. |
| RE34,871 E | 3/1995 | McGuire et al. |
| 5,464,929 A | 11/1995 | Bezwada et al. |
| 5,468,253 A | 11/1995 | Bezwada et al. |
| 5,480,403 A | 1/1996 | Lee et al. |
| 5,562,669 A | 10/1996 | McGuire |
| 5,571,184 A | 11/1996 | DeSatnick |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,645,850 A | 7/1997 | Bezwada et al. |
| 5,648,088 A | 7/1997 | Bezwada et al. |
| 5,690,676 A | 11/1997 | DiPoto et al. |
| 5,698,213 A | 12/1997 | Jamiolkowski et al. |
| 5,700,583 A | 12/1997 | Jamiolkowski et al. |
| 5,707,395 A | 1/1998 | Li |
| 5,733,307 A | 3/1998 | Dinsdale |
| 5,859,150 A | 1/1999 | Jamiolkowski et al. |
| 6,152,928 A | 11/2000 | Wenstrom, Jr. |
| 6,214,007 B1 | 4/2001 | Anderson |
| 6,267,767 B1 | 7/2001 | Strobel et al. |
| 6,306,138 B1 | 10/2001 | Clark et al. |
| 6,379,361 B1 | 4/2002 | Beck, Jr. et al. |
| 6,508,830 B2 | 1/2003 | Steiner |
| 6,579,295 B1 | 6/2003 | Supinski |
| 6,712,849 B2 | 3/2004 | Re et al. |
| 6,887,271 B2 | 5/2005 | Justin et al. |
| 7,201,754 B2 | 4/2007 | Stewart et al. |
| 7,217,279 B2 | 5/2007 | Reese |
| 7,468,074 B2 | 12/2008 | Caborn et al. |
| 8,016,865 B2 | 9/2011 | Donnelly et al. |
| 8,075,588 B2 | 12/2011 | Berberich et al. |
| 2006/0095130 A1* | 5/2006 | Caborn ............... A61F 2/0811 623/13.14 |
| 2006/0253119 A1 | 11/2006 | Berberich et al. |
| 2010/0076504 A1 | 3/2010 | McNamara et al. |
| 2010/0114323 A1* | 5/2010 | Deruntz ............. A61B 17/1675 623/20.21 |
| 2010/0217266 A1* | 8/2010 | Helevirta ........... A61B 17/0401 606/76 |
| 2012/0059469 A1 | 3/2012 | Myers et al. |
| 2013/0261677 A1 | 10/2013 | Bouduban et al. |

FOREIGN PATENT DOCUMENTS

| | | | |
|---|---|---|---|
| GB | 1465744 | * | 3/1977 |
| JP | H09-010245 A | | 1/1997 |
| WO | WO-0232345 A2 | | 4/2002 |
| WO | WO-03028591 A1 | | 4/2003 |

OTHER PUBLICATIONS

Cohn et al. "Biodegradable PEO/PLA Block Copolymers." *J. Biomater. Res.* 22(1988):993-1009.

Cohn. "New Tailor-Made Biodegradable Polymeric Biomaterials." *Polymer Preprints.* 30.1(1989):498.

Heller. "Poly(Ortho Esters)." *Handbook of Biodegradable Polymers.* Domb et al., eds. Amsterdam: Hardwood Academic Press. (1997):99-118.

Kemnitzer et al. "Degradable Polymers Derived from the Amino Acid L-Tyrosine." *Handbook of Biodegradable Polymers.* Domb et al., eds. Amsterdam: Hardwood Academic Press. (1997):251-272.

Vandorpe et al. "Biodegradable Polyphosphazenes for Biomedical Applications." *Handbook of Biodegradable Polymers.* Domb et al., eds. Amsterdam: Hardwood Academic Press. (1997):161-182.

European Search Report for Application No. EP14177728, dated Jun. 10, 2015. (6 Pages).

Japanese Office Action for JP App. No. 2014-146703 dated May 29, 2018 (English translation) (4 pages).

* cited by examiner

METHODS AND DEVICES FOR POSITIONING AND SECURING LIGAMENT GRAFTS

CROSS REFERENCE

The present application claims priority to U.S. Provisional Application No. 61/847,900 entitled "Methods And Devices For Positioning And Securing Ligament Grafts" filed Jul. 18, 2013, which is hereby incorporated by reference in its entirety.

FIELD

The present invention relates to methods and devices for positioning and securing ligament grafts.

BACKGROUND

Ligaments are the fibrous tissue that connects bones to other bones within the body. When ligaments are damaged, surgical reconstruction can be necessary, as the ligaments may not regenerate on their own. One example is a knee 100 shown in FIG. 1, which includes anterior and posterior cruciate ligaments 102, 104 extending from a head of a tibia 106 to an intercondylar notch of the femur 108. These ligaments 102, 104 operate to prevent forward and backward relative motion between the two bones 106, 108. When ruptured (e.g., as can happen in strenuous athletic movements), surgical reconstruction can be necessary.

Tears in the cruciate ligaments of the knee can be repaired using a ligament graft taken from a cadaver (i.e., an allograft) or from a patient's own tissue (i.e., an autograft). Surgeons can reconstruct a cruciate ligament using either a ligament graft from a hamstring, or using a so-called "bone tendon bone" graft that harvests a portion of a patellar tendon 110 (along with plugs of bone at either end from a patella 112 and the tibia 106). More recently, the use of hamstring tissue for ligament grafts has grown more popular.

Reconstruction procedures generally involve forming a hole in both the femur and tibia, and then securing opposite ends of the ligament graft in these holes using an interference screw. One common technique, illustrated in FIG. 2 and known as the "high noon" approach, involves drilling a straight-line hole through the tibia from an inferior medial (i.e., lower and inner) surface thereof and extending almost straight upward through the femur (as shown by line 202). However, this technique can be disadvantageous in that it does not place the ligament graft in the ideal anatomical location, and therefore suffers reduced biomechanical effectiveness.

Another common technique for reconstruction of the cruciate ligaments is known as the "anteromedial" approach. As illustrated in FIG. 3, this technique involves forming a hole in the tibia 106 as described above, but the hole does not extend into the femur 108. Rather, a second hole is formed in the femur 108 along an anteromedial axis 302 of the femur 108. In particular, a hole is formed by drilling into a lateral condyle 304 of the femur 108 from a medial (i.e., inner) surface thereof. This technique can also have disadvantages, however. For example, approaching the lateral condyle 304 along the anteromedial axis 302 can pose a significant risk of contacting and damaging cartilage on a surface of a medial condyle 306. Furthermore, there is often no way to visualize the approach from within the knee (e.g., to assure the medial condyle 306 is not contacted).

A third technique for reconstruction of the cruciate ligaments is known as the "outside in" approach, and involves forming a hole in the femur 108 along the anteromedial axis 302 extending from a lateral surface of the femur 108 (i.e., entry point coming from the opposite of the "anteromedial" approach described above). To date, however, this approach has been mainly limited in that only "bone tendon bone" ligament grafts could be used—the use of increasingly popular hamstring ligament grafts has been possible only in a few limited cases.

Accordingly, there is a need for improved devices and methods for positioning and securing ligament grafts.

SUMMARY

An implant for securing a ligament graft is provided that in one embodiment includes a body having a conical outer profile extending along a longitudinal axis thereof between a proximal end of the body and a tapered distal end of the body. The body can include a first set of opposed slots formed in an outer surface thereof that extend along the longitudinal axis and a transverse slot formed in the proximal end that extends between the first set of opposed slots, and can include a bore formed through the body that is transverse to the longitudinal axis and angularly offset from the first set of opposed slots.

The implant can vary in any number of ways. For example, the body can further include a second set of opposed slots formed in the outer surface thereof that extend from first and second bore holes in the outer surface to the proximal end of the body. For another example, the distal end of the body can be substantially flat. For yet another example, outer edges of the body can be radiused. For another example, the body can be formed from tricalcium phosphate. For still another example, the body can be formed from a polymer.

In another aspect, a system for positioning and securing a ligament graft is provided that in one embodiment includes an implant and a reamer. The implant can have a conical outer profile and a groove formed therein that extends along a longitudinal axis of the implant and around a proximal end thereof. The groove can be configured to seat a middle portion of a ligament graft such that opposed ends of the ligament graft extend beyond a distal end of the implant. The reamer can include a distal portion having a conical outer profile that matches the implant. The reamer can be configured to form a conical hole in bone that is configured to accept the implant.

The implant can have any number of variations. For example, the implant can further include a bore formed through the implant that is transverse to the longitudinal axis and angularly offset from the groove. The implant can further include opposed slots formed in an outer surface thereof that extend between first and second bore holes and the proximal end of the implant. The system can also include a suture length passed through the bore such that opposed ends of the suture length extend beyond the proximal end of the implant.

The reamer can vary in any number of ways. For example, the reamer can include at least one depth marking configured to indicate a size of the conical hole formed. For another example, the reamer can include a handle at a proximal end thereof configured to manually actuate the reamer.

In another aspect, a method for positioning and securing a ligament graft is provided that in one embodiment includes forming a conical bore through a femur that tapers from an outer surface of the femur toward an inner surface of the femur, forming a bore through a tibia that extends from an inner surface of the tibia to an upper surface of the tibia, preparing a ligament graft by wrapping a middle portion of the ligament graft around an implant having a conical outer profile such that the ligament graft is received in a groove formed around an outer surface of the implant and opposed ends of the ligament graft extend beyond a distal end of the implant, introducing the opposed ends of the ligament graft through the conical bore from the outer surface of the femur and then through the bore in the tibia from the upper surface thereof, and securing the ligament graft such that the conical outer profile of the implant form fits within the conical bore in the femur.

The method can have any number of variations. For example, the conical bore can be formed along an anteromedial axis of the femur. For another example, the conical bore can be formed using a reamer having a conical distal portion. For yet another example, the reamer can be actuated by hand. For another example, the method can include securing the opposed ends of the ligament graft in the bore in the tibia. For still another example, the method can include rotating the implant and the ligament graft prior to the securing of the ligament graft. For another example, forming the conical bore can include sizing the bore such that a distal end of the implant sits flush with the inner surface of the femur when the implant is secured in the conical hole. For yet another example, the method can include securing the implant by passing a suture through a bore formed therein and then through a second bore formed in the femur.

BRIEF DESCRIPTION OF THE DRAWINGS

The aspects and embodiments of the invention described above will be more fully understood from the following detailed description taken in conjunction with the accompanying drawings, in which.

DETAILED DESCRIPTION

Figure 1:
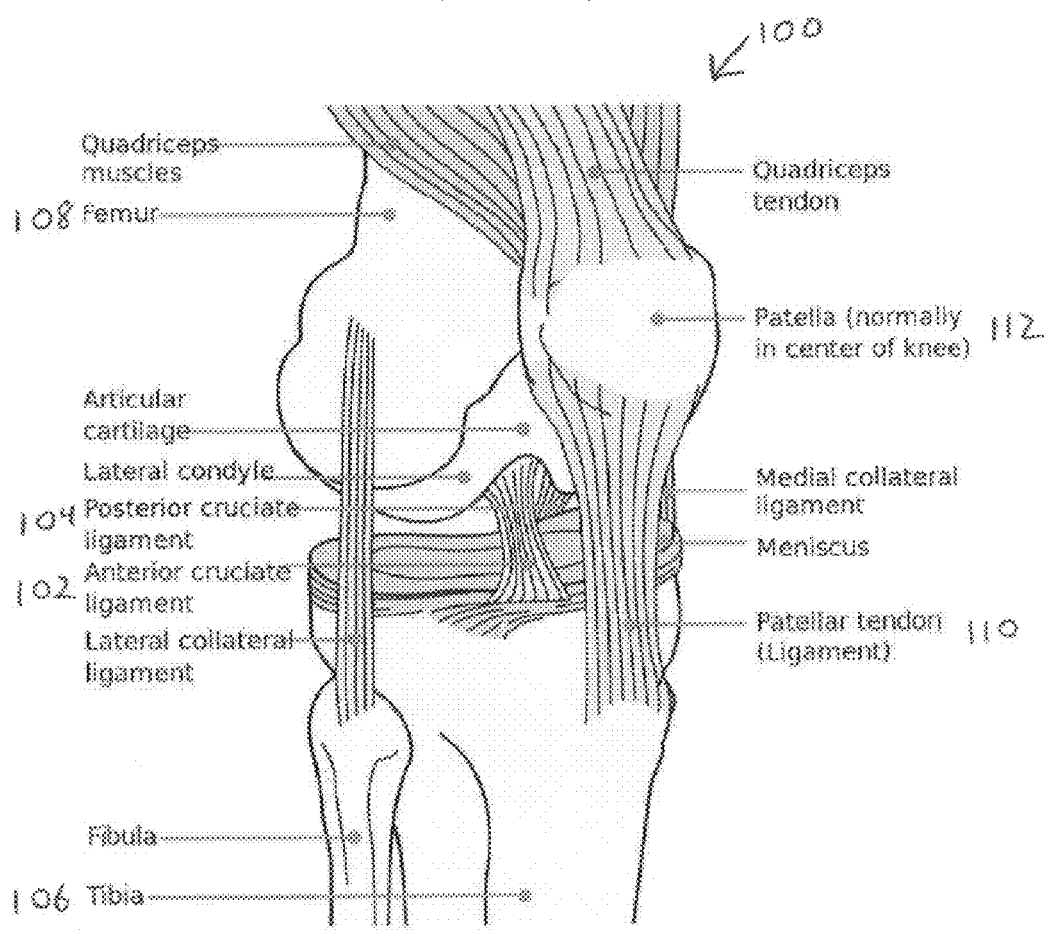
FIG. 1 (Prior Art) is an illustration of anatomy of a human knee.
Figure 2:
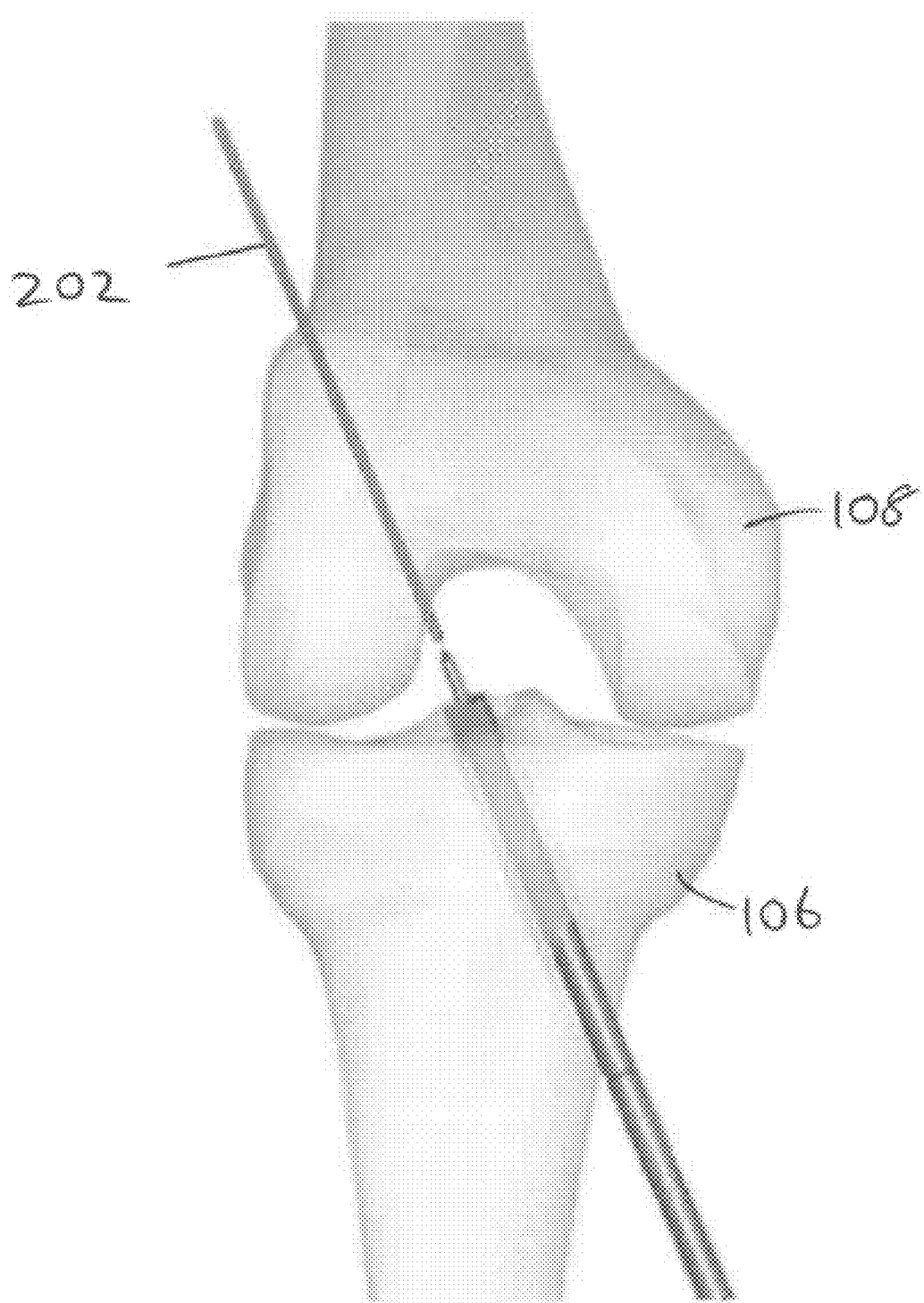
FIG. 2 is an illustration of one prior art approach to cruciate ligament reconstruction surgery.
Figure 3:
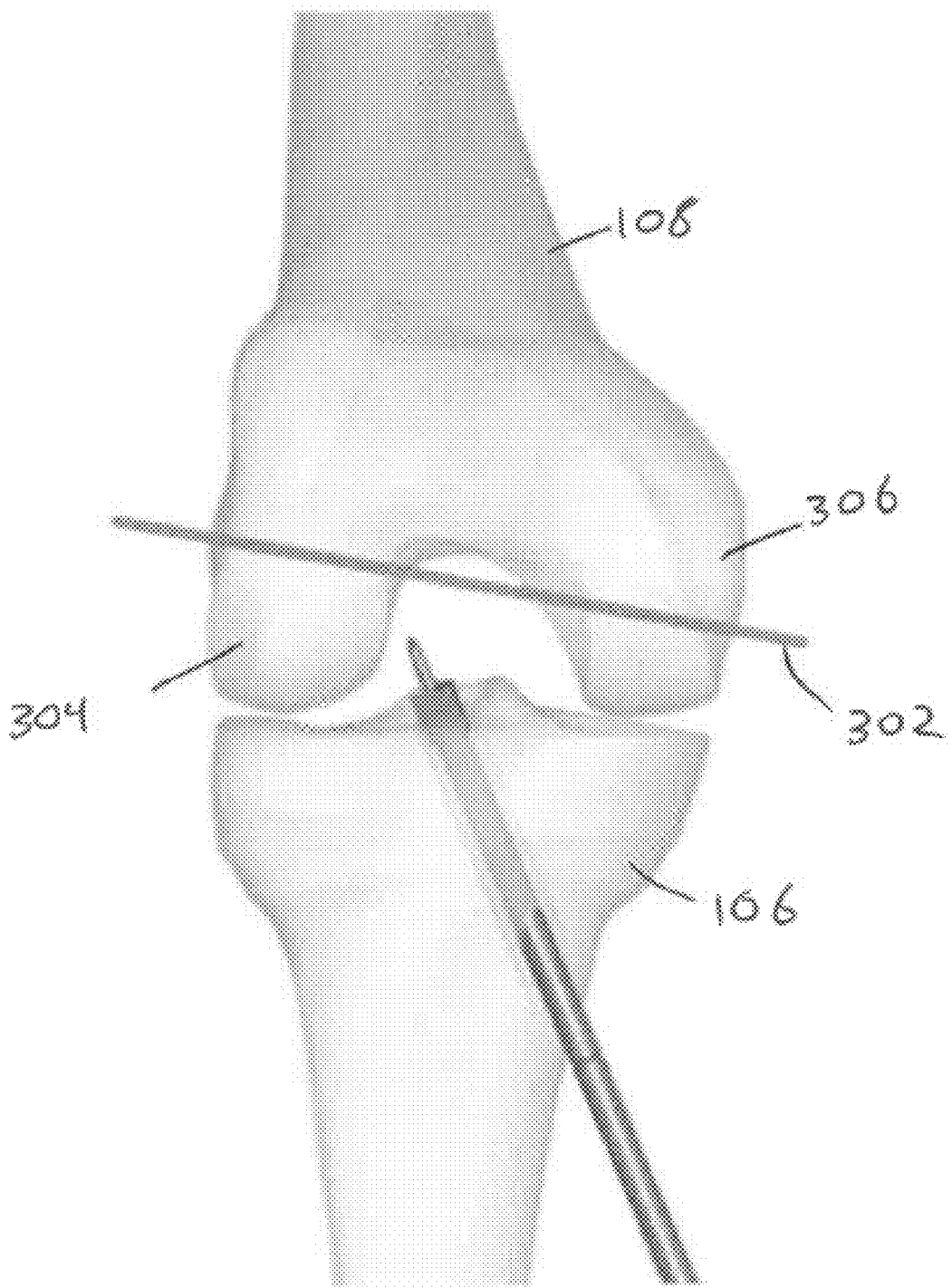
FIG. 3 is an illustration of an alternative prior art approach to cruciate ligament reconstruction surgery.
Figure 4A:
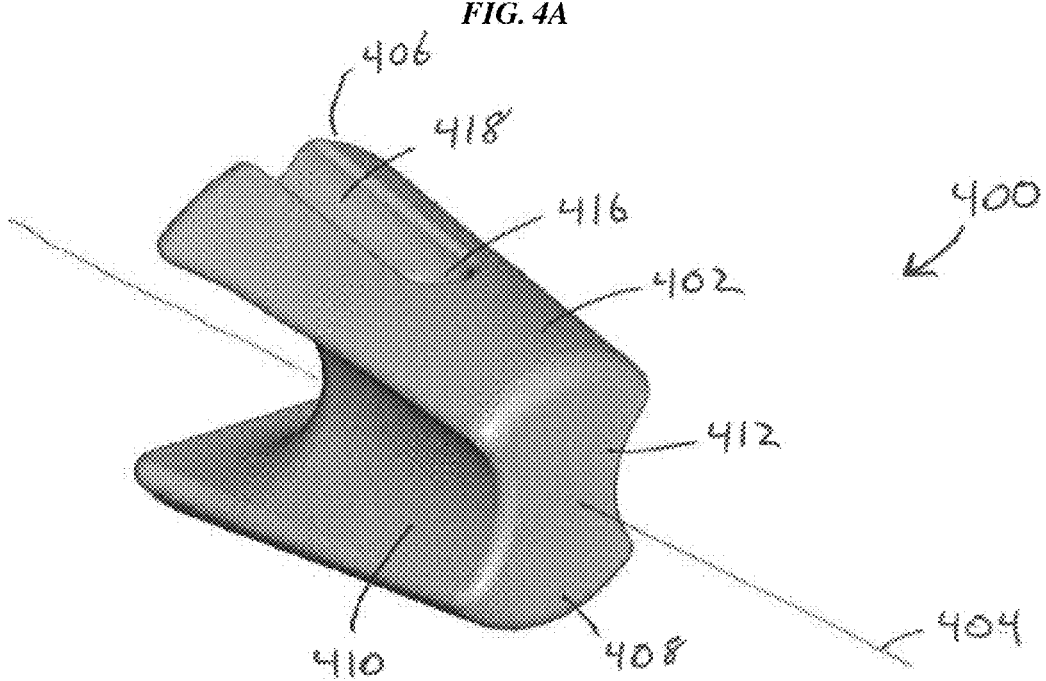
FIG. 4A is a front isometric view of one embodiment of an implant.
Figure 4B:
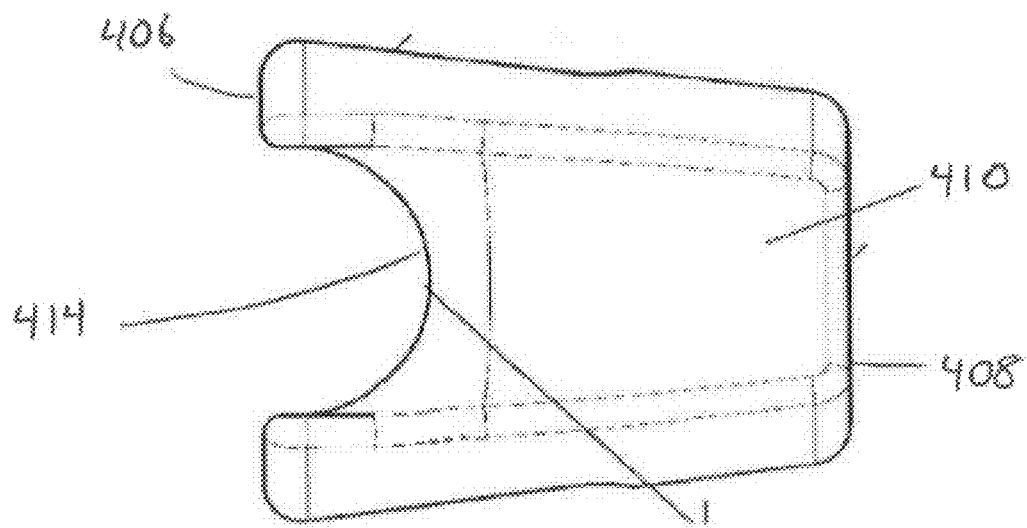
FIG. 4B is a side view of the implant of FIG. 4A.
Figure 4C:
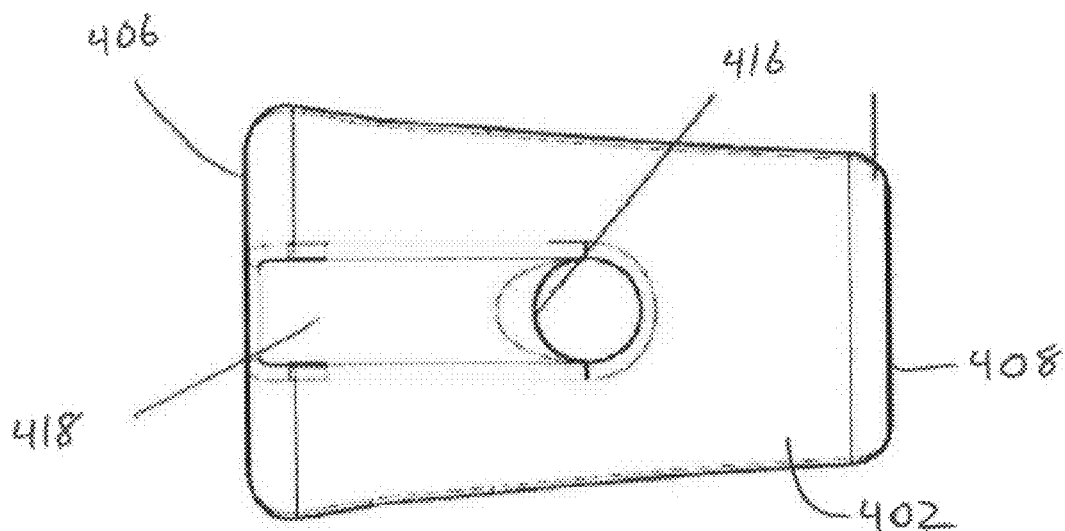
FIG. 4C is a top view of the implant of FIG. 4A.
Figure 4D:
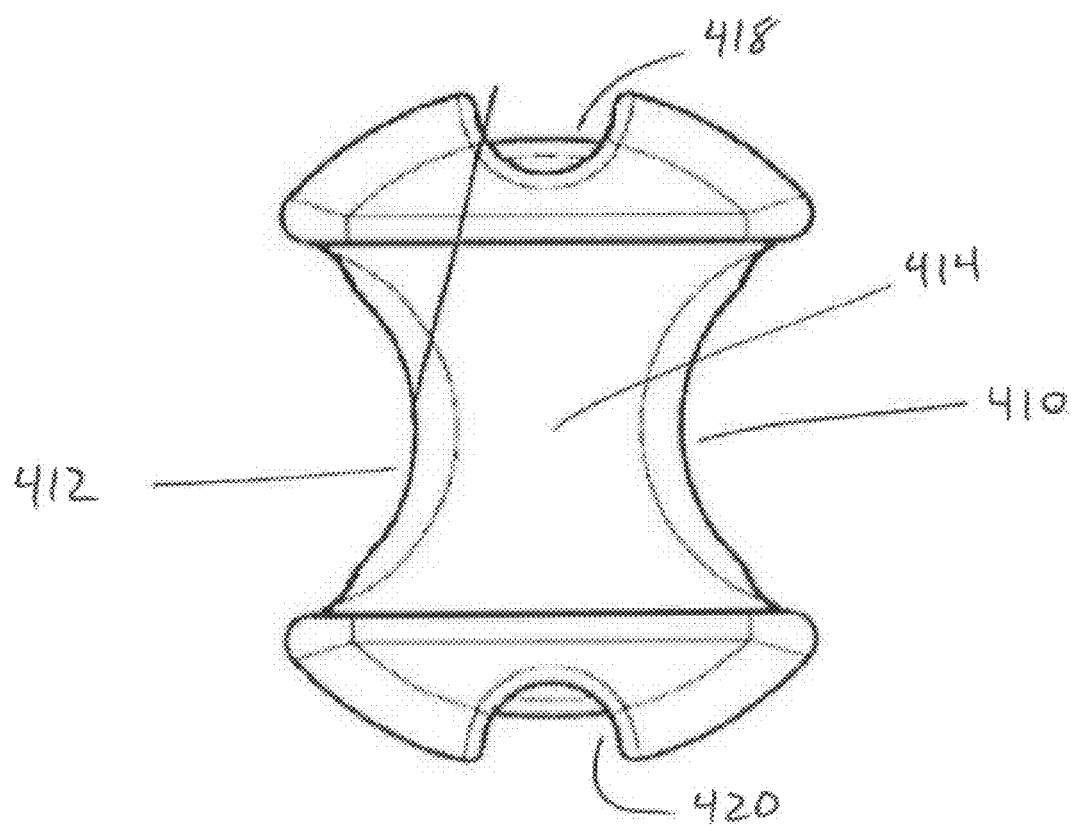
FIG. 4D is a rear view of the implant of FIG. 4A.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. Further, the features illustrated or described in connection with one exemplary embodiment may be combined with the features of other embodiments. Such modifications and variations are intended to be included within the scope of the present invention.

The present invention is generally directed to methods and devices for positioning and securing ligament grafts. In particular, the devices and methods described herein utilize an implant having a particular outer surface profile and a bone tunnel having a complementary profile to provide a form fit between the implant and bone that utilizes friction to position and secure a ligament graft within the bone. Such an implant can be used in conjunction with a variety of ligament grafts, including hamstring ligament grafts. In addition, an "outside in" approach can be utilized with the implant to minimize the risk of damaging adjacent tissue during an operation and provide enhanced surgeon control. The devices and methods described herein can allow for the use of various types of ligament grafts including, for example, hamstring ligament grafts, which can facilitate use of the devices and methods in a variety of different surgical contexts regardless of the type of ligament graft being used in a particular surgical procedure. The devices and methods described herein can allow a ligament graft to be placed in the ideal anatomical location and therefore provide biomechanical effectiveness. The devices and methods described herein can reduce, if not entirely eliminate, risk of contacting and damaging cartilage on a surface of a medial condyle of a femur and/or can allow an approach within a patient (e.g., an approach within the patient's knee) to be visualized. Such visualization can help assure that the patient's anatomy is not damaged, such as by helping to assure that the patient's medial condyle is not contacted in an approach involving the patient's knee. The devices and methods described herein can be utilized in connection with repairing or replacing ligaments in a variety of joints, but can in some embodiments have particular utility in cruciate ligament reconstruction procedures. In some embodiments, the devices and methods described herein can be utilized in reconstruction procedures that include, for example, the cruciate ligaments of the knee.

The methods and devices described herein have a number of advantages over prior art techniques for positioning and securing ligament grafts. For example, a friction form fit that is provided by mating an implant and a bone hole having complementary conical shapes can provide superior graft fixation, bone hole or tunnel sealing, graft preservation, and bone integration when compared to other methods for fixing a graft to bone. In particular, superior fixation and hole sealing can prevent loosening of a graft over time due to, for example, "bungee" or "windshield wiper" effects. Graft preservation can be improved by using an implant having radiused edges, and bone integration can be improved by using particular biocompatible materials, such as tricalcium phosphate (TCP). In addition, a number of interference screws necessary to perform a given procedure is reduced.

Furthermore, and in particular reference to cruciate ligament reconstruction procedures, the "outside in" approach afforded by the implants described herein allows for a more controlled operation with less risk of damaging adjacent cartilage or other components of the knee. This is due in part to the ability to directly visualize the creation of a femoral bone tunnel or hole from within the knee. Under this direct visualization, surgeons can effectively ensure that the hole is placed in the correct location and has the correct size such that, e.g., an implant's distal end sits flush with the surface of the bone when implanted, thereby sealing the hole properly.

The implants described herein permit the use of a variety of ligament grafts, including hamstring grafts, in combination with an "outside in" approach. Of course, other ligament grafts, such as bone tendon bone or quadriceps grafts, can also be used. A size of the implant, and the corresponding size of the conical bone hole, can be adjusted as necessary for any particular ligament graft.

The implants described herein can be formed from a biocompatible material that promotes bone integration such that the patient's body will grow around and even through the implant over time. For example, the implant can be composed of a suitable copolymer combination, such as polylactic acid-polyglycolic acid (PLA-PGA), with a predominant fraction of PGA. Other bioabsorbable polymers can also be used. Examples of suitable biocompatible, bioabsorbable polymers include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, (-valerolactone, &-butyrolactone, (-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and ,-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Exemplary bioabsorbable, biocompatible elastomers include but are not limited to elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of εcaprolactone and p-dioxanone where the mole ratio of ,-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof.

Examples of suitable bioabsorbable elastomers are described in U.S. Pat. Nos. 4,045,418; 4,057,537 and 5,468,253.

In other embodiments, the implants described herein can be formed from polylactic acid, or a composite blend of TCP and polylactic acid. An example is the combination of TCP and poly lactic-co-glycolic acid (PLGA) sold as Biocryl Rapide™ from DePuy Mitek, Inc. Still other examples of biocompatible polymers can include poly-ether-ether-ketone (PEEK), polyglycolic acid, and combinations thereof. It is also contemplated that the implants described herein can be made of non-absorbable materials. For example, the implants described herein may be made of polysulfone, or a metal such as Titanium 6A1-4V or stainless steel. In yet other embodiments, the implants described herein can be formed from bone harvested from the patient or a donor source.

FIGS. 4A-4D illustrate various views of one embodiment of an implant 400. As in this illustrated embodiment, a body of the implant can have a conical outer profile, that is, an outer surface 402 of the implant body can approximate the shape of a cone as it extends along a longitudinal axis 404 of the implant 400 from a proximal end 406 of the implant 400 to a tapered distal end 408 of the implant 400. The outer surface 402 can be configured to engage with complementary conical inner walls of a bone hole formed in a bone such that the implant 400 can be securely friction fit into the bone hole to secure a ligament graft, as discussed further below. In other words, the conically shaped outer surface 402 can be configured to facilitate the friction fit between the implant 400 and the bone.

The implant 400 can also include a first set of opposed slots 410, 412 formed in the outer surface 402 that extend along the longitudinal axis 404. In addition, a transverse slot 414 can be formed in the proximal end 406 and can extend between the opposed slots 410, 412. The three slots 410, 412, 414 together can form a saddle-like shape extending around three sides of the implant 400 such that a ligament graft can be looped around the implant 400 and seated within the slots 410, 412, 414, as described below. The slots 410, 412, 414 can each have a variety of sizes (e.g., depths and widths) according to a size of the implant 400 and intended type of ligament graft. For example, in some embodiments, a width of each of the slots 410, 412, 414 can encompass an angle in a range of about 1° and about 89° of the conical outer surface 402.

The distal end 408 of the implant 400 can be substantially flat such that the distal end 408 can be configured to sit flush with a surface of a bone when the implant 400 is form fit into a conical bone hole or bore, as discussed further below. Furthermore, as in this illustrated embodiment, all edges of the implant 400 can be radiused to minimize sharp edges that can wear a ligament graft or surrounding bone or tissue over time.

The implant 400 can also include a bore 416 formed therethrough that is transverse to the longitudinal axis 404 and angularly offset from the first set of opposed slots 410, 412. In the illustrated embodiment, the bore 416 is shown in a perpendicular (i.e., 90° angular offset) orientation relative to the first set of opposed slots 410, 412. The angular orientation between the first set of opposed slots 410, 412 and the bore 416 can be varied and, in certain embodiments, it can be preferable to avoid very small angular offsets that can place the bore 416 within the first set of opposed slots 410, 412.

The bore 416 can be configured to receive a suture length (not shown) such that opposed ends of the suture length extend beyond the proximal end 406 of the implant 400. The opposed ends of the suture length can then be used to remove, rotate, or otherwise re-approximate the implant 400 after it is placed within a bone hole. In addition, the opposed ends of the suture length can be used to redundantly secure the implant 400 within the bone hole should the friction form fit ever give out.

The bore 416 can allow the implant 400 to be placed within the bone hole using the suture length such that no instrument need be introduced into the bone hole to place the implant 400 therein. Thus, the bore 416 can facilitate reduction of a number of instruments needed to perform a surgical procedure and/or can reduce chances of damaging adjacent cartilage and/or other material since no instrument need be advanced into the bone hole for implant placement.

The implant 400 can include a second set of opposed slots 418, 420 formed in the outer surface 402. The second set of opposed slots 418, 420 can extend from first and second bore holes (best shown in FIG. 4C) in the outer surface 402 (formed at either end of the bore 416) to the proximal end 408 of the implant body. The second set of opposed slots 418, 420 can be configured to seat a suture length such that the suture length does not protrude above the outer surface 402. The opposed slots 418, 420 can thus be configured to prevent the suture length extending through the bore 416 from interfering with the friction form fit of the implant 400 within a bone hole.

Figure 5A:
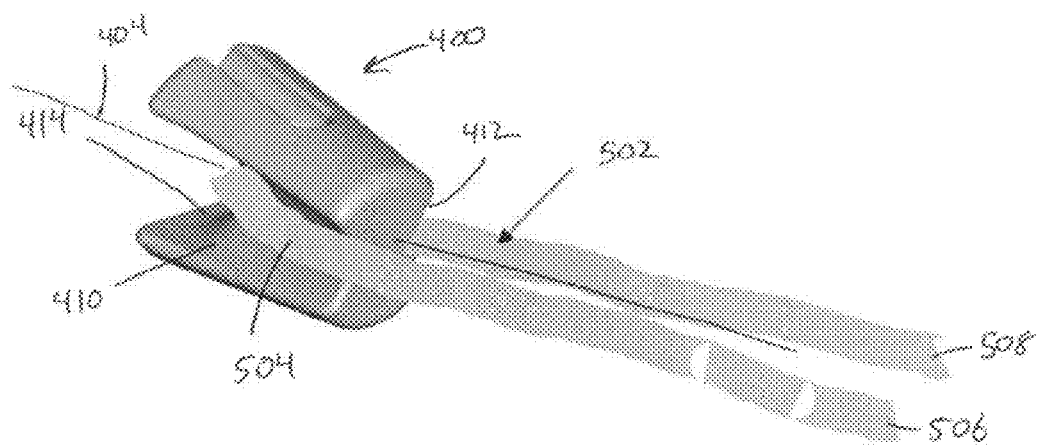
FIG. 5A is a front isometric view of one embodiment of a ligament graft and the implant of FIG. 4A.
Figure 5B:
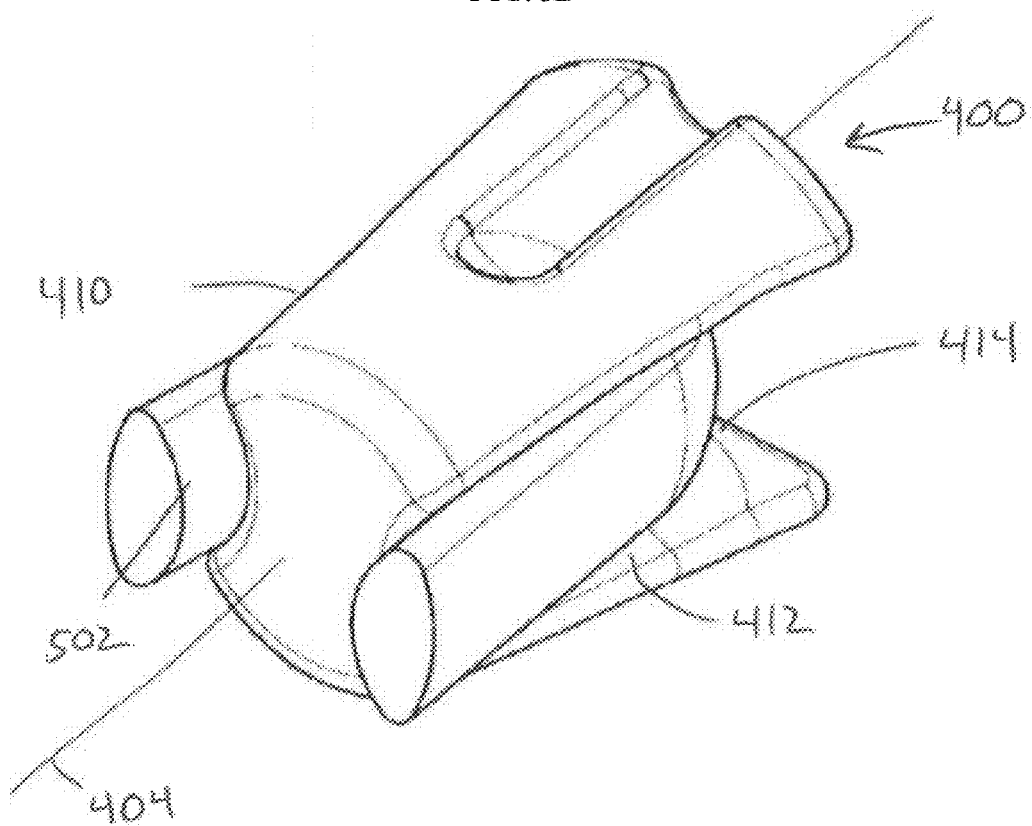
FIG. 5B is an alternative view of the ligament graft and implant of FIG. 5A.

FIGS. 5A and 5B illustrate alternative views of the implant 400 and an exemplary embodiment of a ligament graft 502 (e.g., a hamstring ligament graft). As shown in FIGS. 5A and 5B, the first set of opposed slots 410, 412 and the transverse slot 414 form an uninterrupted groove that extends along the longitudinal axis 404 and around the proximal end 406 of the implant 400. This groove can be configured to seat a middle portion 504 of the graft 502 such that opposed ends 506, 508 of the ligament graft 502 extend beyond the distal end 408 of the implant 400, as shown in FIGS. 5A and 5B.

Figure 6:
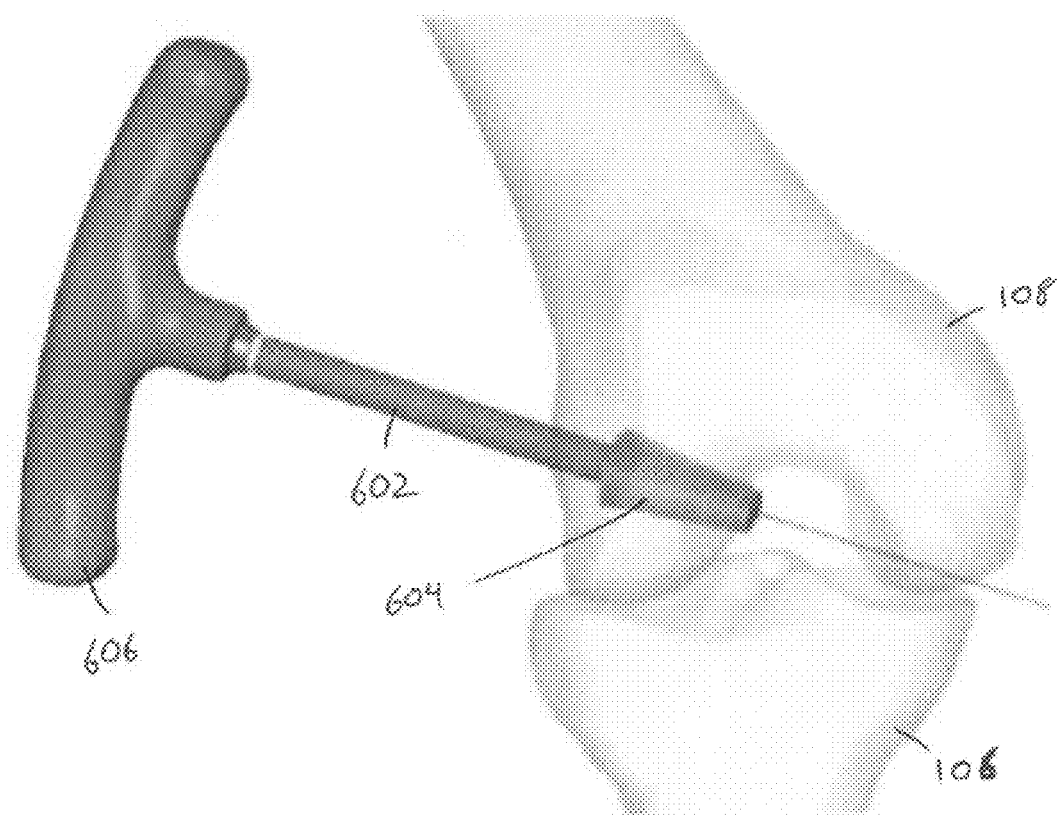
FIG. 6 is an illustration of one embodiment of a reamer.

Such a configuration can provide very secure fixation of the ligament graft 502 when the implant 400 is placed within a bone hole having a complementary inner profile to the outer surface 402 of the implant 400. As shown in FIG. 6, a bone hole having a complementary inner profile can be created in some embodiments using a reamer 602 with a distal portion 604 that has a conical outer profile. The conical outer profile of the distal portion 604 of the reamer 602 can match the conical outer profile of the outer surface 402 of the implant 400. The matching conical outer profiles can facilitate correct placement of the implant 400 to an aperture (joint surface) and/or can help create optimal fixation with strength. The conical outer profiles can be matched by the distal portion 604 of the reamer 602 having an angle that is no smaller than an angle of the outer surface 402 of the implant 400. The angle of the distal portion 604 can thus be substantially the same as or be greater than the angle of the outer surface 402. A person skilled in the art will appreciate that the angles of the distal portion 604 and the outer surface 402 may not be exactly the same but nevertheless be considered to be substantially the same due to, e.g., manufacturing tolerances. In an exemplary embodiment, the angle of the distal portion 604 can thus be substantially the same as or be slightly greater than the angle of the outer surface 402, which can facilitate very secure fixation of the implant 400 within the bone hole created by the reamer 602.

The conical outer profile of the distal portion 604 of the reamer 602 can include features formed thereon to remove and shape bone upon actuation (e.g., rotation).

The distal portion 604 of the reamer 602 can also include one or more depth markings (not shown in FIG. 6) formed thereon such that a user can gauge the size of the conical hole being formed. This can be important in order to form a hole that exactly matches the outer dimensions of the implant 400 such that a secure friction form fit can be achieved. At a proximal end of the reamer 602, a handle 606 or other driving mechanism can be coupled thereto. Exemplary driving mechanisms can include electric drills, compressed air or liquid sources, etc. In certain embodiments, a handle can be preferred to give a surgeon precise feedback and control over the amount of bone removed from the bone hole.

Figure 7:
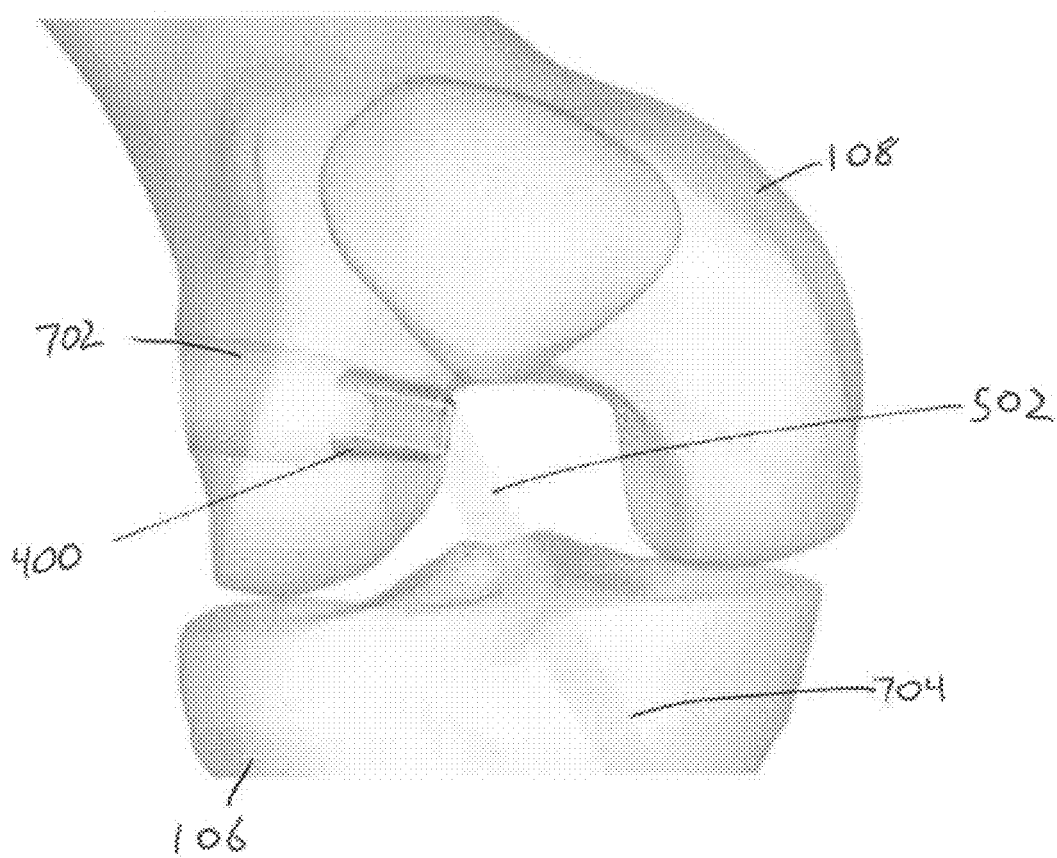
FIG. 7 is an illustration of one embodiment of the implant of FIG. 4A form fit into a conical hole formed in a femur.

FIG. 7 illustrates one embodiment of the implant 400 and the ligament graft 502 positioned within a conical bone hole 702. In the illustrated view, the implant 400 and the ligament graft 502 are positioned in the conical bone hole 702, which is formed in a lateral (i.e., outer) portion of a femur 108. The ligament graft 502 extends out of the conical bone hole 702 at its medial end and into a bone hole 704 formed in a tibia 106. The ligament graft 502 can be secured in the bone hole 704 of the tibia 106 using, for example, an interference screw. The friction form fit of the implant 400 in the conical bone hole 702 can securely fix the ligament graft 502 to the femur 108, such that the ligament graft 502 can function as a replacement for one of the cruciate ligaments of the knee (e.g., in the illustrated embodiment, the ligament graft 502 is in the position of the anterior cruciate ligament, or ACL).

Figure 8A:
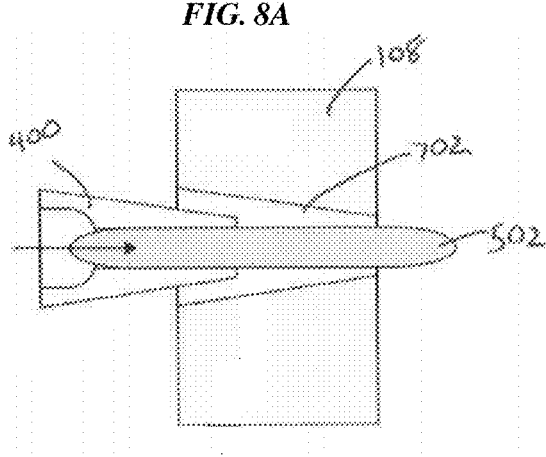
FIG. 8A is a schematic illustration of one embodiment of the implant of FIG. 4A and the ligament graft of FIG. 5A being introduced into the conical hole of FIG. 7.
Figure 8B:
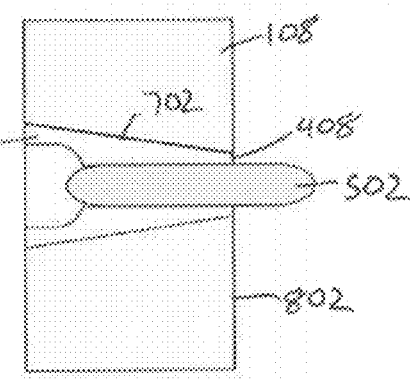
FIG. 8B is a schematic illustration of the implant and ligament graft of FIG. 8A form fitted into the conical hole of FIG. 8A.
Figure 8C:
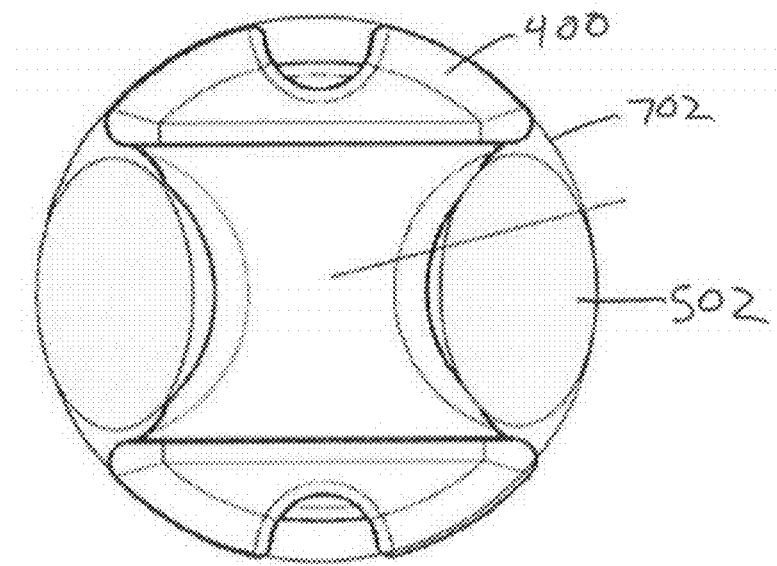
FIG. 8C is a front view of the implant and ligament graft of FIG. 8A.

FIGS. 8A-8C illustrate in detail the friction form fit of the implant 400 and the conical bone hole 702. As shown in FIG. 8A, the ends 506, 508 of the ligament graft 502 can be introduced into the bone hole 702 first from a lateral (i.e., outer) side of the femur 108. In some embodiments, graspers or other manipulation tools can be used to pull the opposed ends 506, 508 through the bone hole 702 from the tapered end. The implant 400 enters the bone hole 702 and travels through the hole 702 until the outer surface 402 of the implant 400 abuts against inner walls of the bone hole 702, as shown in FIG. 8B.

It can be important to size the bone hole 702 appropriately such that the implant 400 becomes locked in place at a point where the distal end 408 of the implant 400 sits flush with the surface of the bone 802 at the tapered end of the hole 702, as shown in FIG. 8B. Seating the implant 400 in such a configuration can seals the bone hole 702 completely, as shown in the rear view of FIG. 8C. Without complete sealing of the bone hole 702, the implant 400 can loosen over time due to "bungee" or "windshield wiper" effects. The bungee effect occurs when the ligament graft 502 is stretched too much over the implant 400 without proper support from sidewalls of the bone tunnel 702. The unsupported stretching can lengthen and weaken the ligament graft 502. The windshield wiper effect, on the other hand, occurs when incomplete sealing allows synovial fluid from the knee joint to fill the bone tunnel 702. Movement of this fluid through the tunnel 702 can slowly erode the tunnel walls at the tapered end. In addition, oscillating movement of the ligament graft 502 (similar to movement of a car's windshield wiper) in a loose bone tunnel can further contribute to erosion of the bone hole walls, cause damage to the graft 502 itself, and loosen the fixation of the graft 502 and the implant 400. By sealing the bone hole 702, these problems can be avoided.

The implant 400 and the ligament graft 502 can be rotated prior to fixation, which can achieve the best biomechanical positioning of the ligament graft 502 (e.g., the best orientation of the two bundles that lead to the opposed ends 506, 508 of the ligament graft 502). After the desired rotational orientation is selected, the friction form fit of the implant 400 within the bone hole 702 can prevent any future rotation without further action.

Figure 9A:
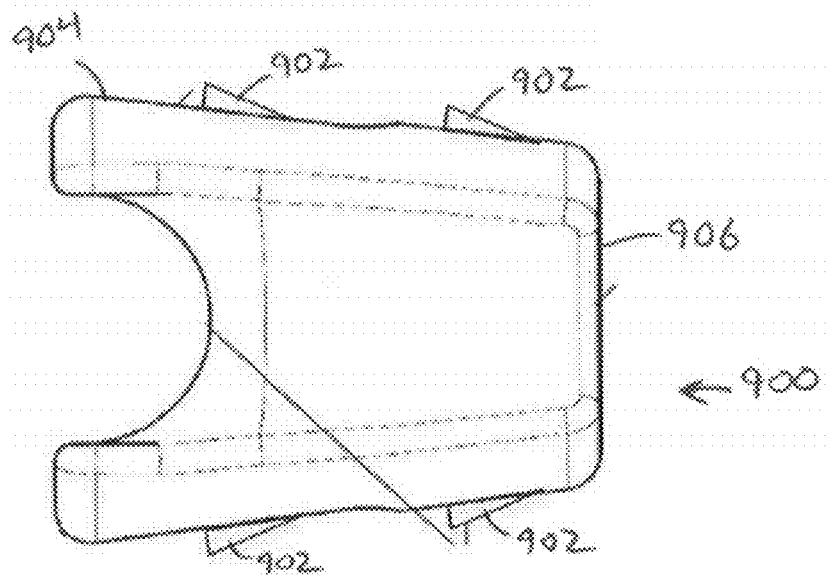
FIG. 9A is a side view of an alternative embodiment of an implant.
Figure 9B:
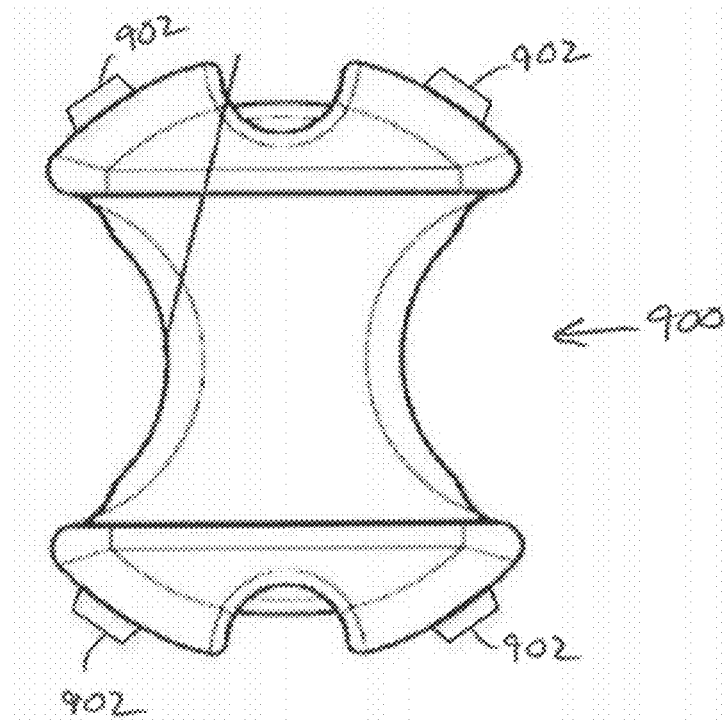
FIG. 9B is a rear view of the implant of FIG. 9A.

In cases where additional support is desired, an outer surface of an implant can include one or more surface features configured to inhibit rotational (or axial) movement of the implant. In use, the one or more surface features can protrude into bone surrounding the implant and provide additional support to the friction form fit between the implant and the bone tunnel. FIGS. 9A and 9B illustrate one embodiment of such surface features. Shown in FIGS. 9A and 9B is an implant 900, similar to the implant 400 of FIG. 4A described above, that includes surface features in the form of a plurality of barbs 902 formed on an outer surface 904 thereof. The barbs 902 can be integrally formed of the same material as a body of the implant 900, or the barbs 902 can be separate components (made of the same or a different material) affixed to the implant 900 in any manner known in the art. The barbs 902 can be biased to allow one-way movement (e.g., movement toward a distal end 906 of the implant 900).

Exemplary methods for positioning and securing a ligament graft are also provided. The methods can use the systems and devices described above. In general, an exemplary method can include forming a conical bore through a bone, e.g., a femur, that tapers from an outer surface of the bone toward an inner surface of the bone. The method can further include forming a bore through a second bone, e.g., a tibia, that extends from an inner surface of the second bone to an upper surface of the second bone. A ligament graft can be prepared by wrapping a middle portion of the ligament graft around an implant having a conical outer profile such that the ligament graft is received in a groove formed around an outer surface of the implant and opposed ends of the ligament graft extend beyond a distal end of the implant. The opposed ends of the ligament graft can be introduced through the conical bore from the outer surface of the bone and then through the bore in the second bone from the upper surface thereof. In addition, the method can include securing the ligament graft such that the conical outer profile of the implant form fits within the conical bore in the bone.

FIGS. 10-18 illustrate one embodiment of a method for positioning and securing a ligament graft. In particular, the illustrated embodiment shows a method for reconstructing an anterior cruciate ligament, though the method can be adapted for other ligament repair procedures as well.

Figure 10:
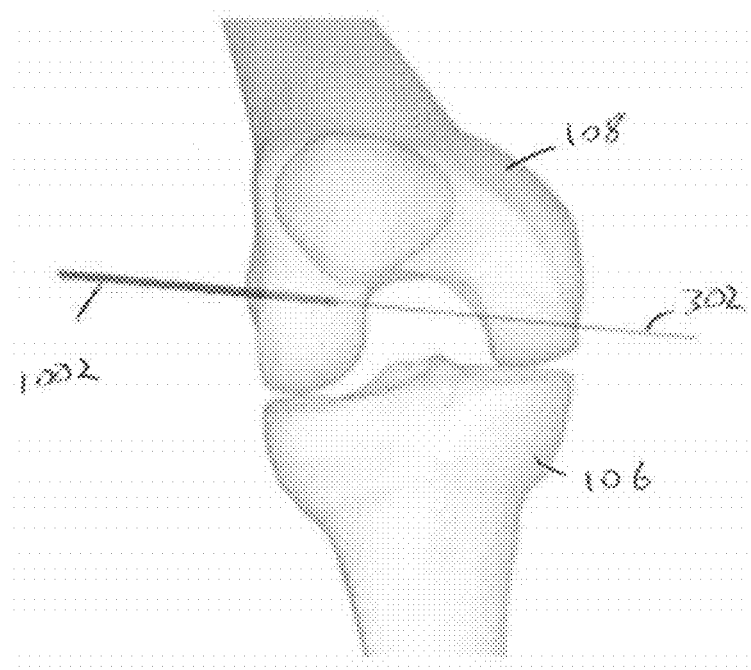
FIG. 10 is an illustration of one embodiment of a technique for introducing a guide wire into a femur.
Figure 11:
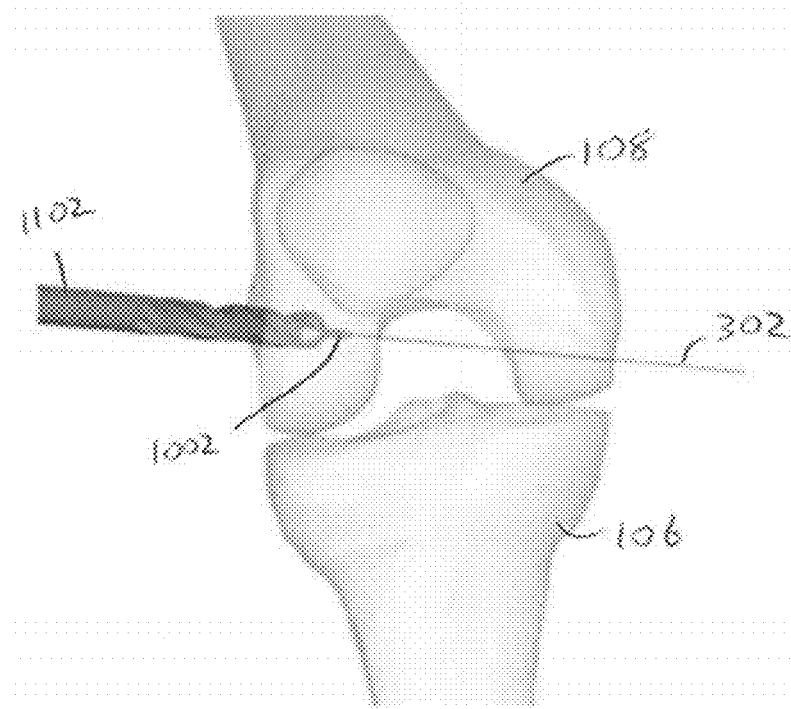
FIG. 11 is an illustration of one embodiment of a technique for forming a hole in the femur of FIG. 10.

FIG. 10 illustrates a first step in the method wherein a K-wire 1002 or other guide wire device is introduced through a patient's femur 108 along an anteromedial axis 302 of the femur 108. In some embodiments, an arthroscopic viewing device (not shown) can be inserted into the patient's knee through a separate incision in a medial (i.e., inner) portion of the joint to view the K-wire 1002 from within the knee. In still other embodiments, a tibia drilling process described below with respect to FIGS. 14 and 15 can be conducted first, and an arthroscopic viewing device (not shown) can be introduced into the patient's knee through a bone hole formed in the tibia 106 to view the K-wire 1002 passing through the femur 108.

After introducing the K-wire 1002, a drill 1102 can be used to form a larger hole through the femur 108 from a lateral (i.e., outer) side of the knee toward a medial (i.e., inner) side. Drilling in this manner (and, in some embodiments, under direct observation from a viewing device (not shown) positioned within the knee) can allow greater control and minimize the risk of damaging adjacent cartilage or other tissue structures.

Figure 12A:
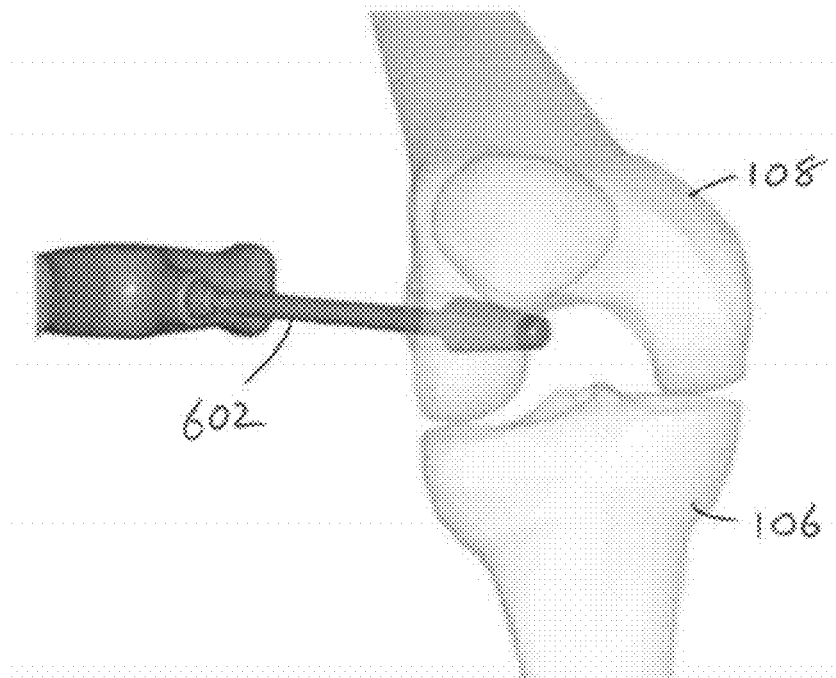
FIG. 12A is an illustration of one embodiment of a technique for forming a conical hole in the femur of FIG. 11.
Figure 12B:
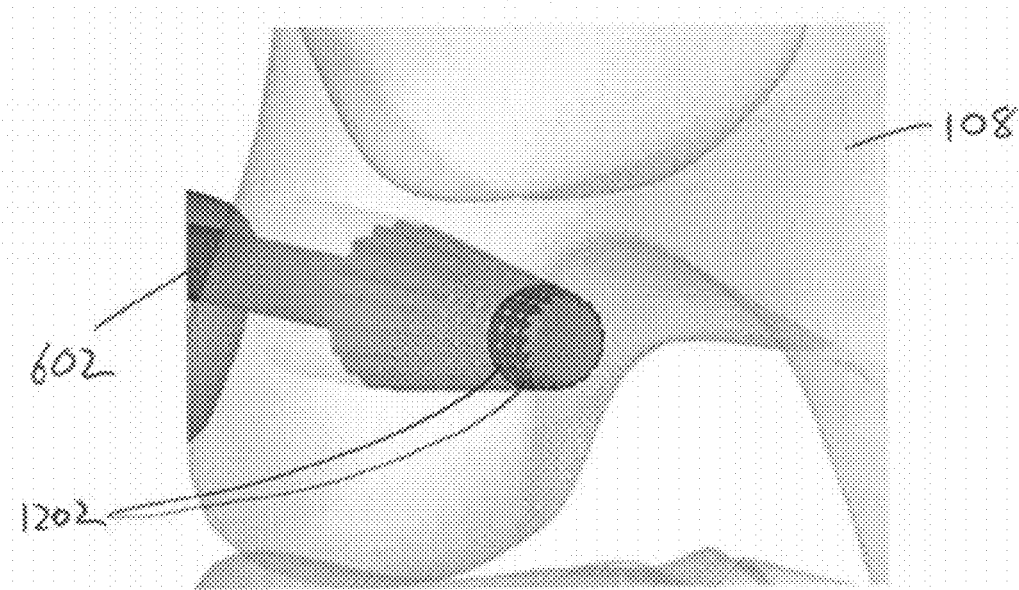
FIG. 12B is a detailed view of a portion of the illustration of FIG. 12A.
Figure 13:
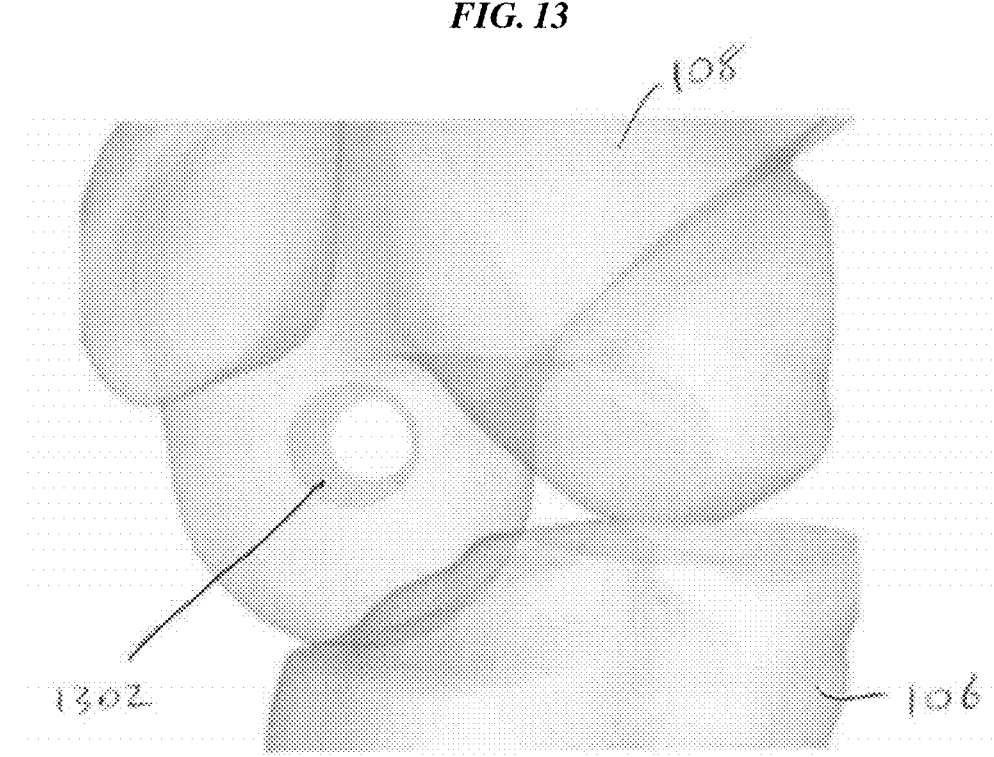
FIG. 13 is an illustration of one embodiment of the conical hole formed in the femur of FIG. 12A.

After forming a straight-line bone hole using the drill 1102, a surgeon can use the reamer 602 to form a conical bone hole 1302 in the femur 108 that tapers from a lateral (i.e., outer) surface of the femur 108 toward a medial (i.e., inner) surface. FIGS. 12A and 12B illustrate this process, and FIG. 13 illustrates the conical bone hole 1302. During use of the reamer 602, a surgeon can visualize the conical hole 1302 being formed from within the knee using the arthroscopic viewing device described above. Accordingly, in some embodiments, the reamer 602 can include one or more depth markings 1202 formed on a distal portion thereof. A surgeon viewing the formation of the conical bone hole 1302 can easily see the depth markings 1202 as they emerge from the bone hole 1302, thereby allowing precise control of the size of the conical hole 1302 formed. This precise control can allow a surgeon to create a conical hole that exactly matches the outer profile of the implant being used. FIG. 13 illustrates the conical hole 1302 formed by the reamer 602 from the lateral (i.e., outer) side of the patient's knee.

Figure 14:
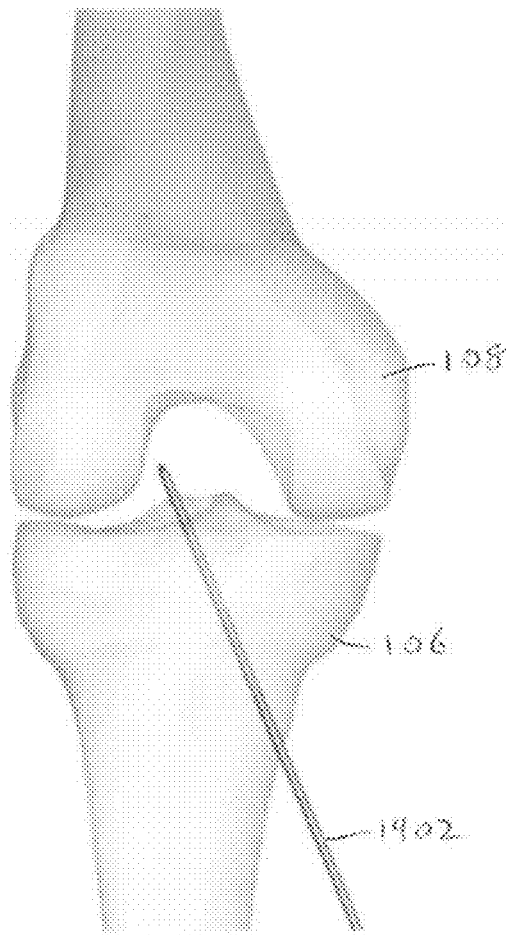
FIG. 14 is an illustration of one embodiment of a technique for introducing a guide wire into a tibia.
Figure 15:
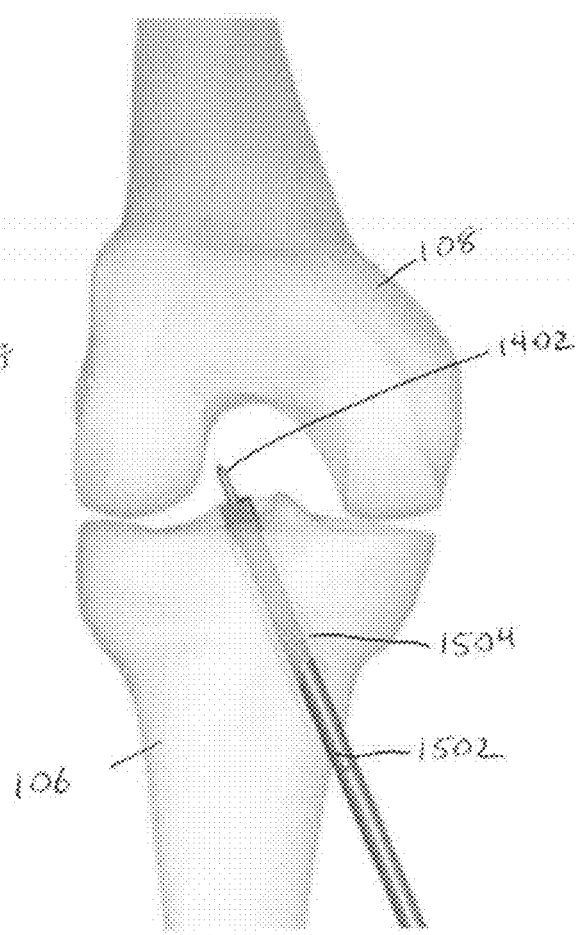
FIG. 15 is an illustration of one embodiment of a technique for forming a hole in the tibia of FIG. 14.

Following (or, in some embodiments, prior to) preparation of the femur 108, a bone hole can be formed in the tibia 106. FIGS. 14 and 15 illustrate one embodiment of forming a straight bone hole 1504 in the tibia 106. This process can begin with the introduction of a K-wire 1402, similar to the process discussed with respect to FIG. 10 above. After introducing the K-wire 1402 from a medial inferior (i.e., inner and lower) portion of the tibia 106 up through a superior (i.e., upper) surface thereof, a drill 1502 can be passed over the K-wire 1402 to form the straight bone hole 1504 in the tibia 106.

Figure 16:
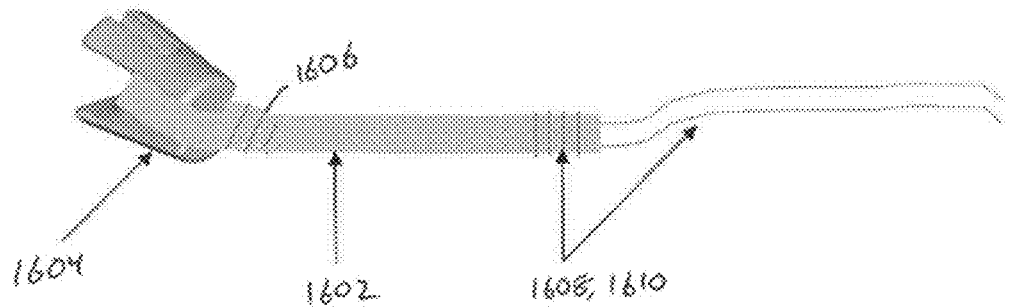
FIG. 16 is an illustration of one embodiment of a ligament graft and implant.

Having prepared both the femur 108 and the tibia 106, a ligament graft can be introduced through the holes 1302, 1504 formed in these bones 108, 106. As shown in FIG. 16, a ligament graft 1602 can be prepared by wrapping a middle portion thereof around an implant 1604, which is similar to the implant 400 of FIG. 4A described above. In order to aid in securing the ligament graft 1602 to the implant 1604 prior to securing the implant 1604 in the conical bone hole 1302, a suture 1606 can be used to tighten the ligament graft 1602 against a distal end of the implant 1604. Additional sutures 1608, 1610 can be affixed to two opposed ends of the ligament graft 1602 that are located adjacent to one another opposite the implant 1604. These sutures 1608, 1610 can be used to aid a surgeon in passing the ligament graft 1602 through the bone holes 1302, 1504 formed in the femur 108 and the tibia 106. Finally, a suture (not shown) can also be passed through a bore (not shown) formed in the implant 1604, similar to the bore 416 of the implant 400 of FIG. 4, which can allow the implant 1604 to be rotated, re-approximated, or withdrawn if necessary.

To introduce the ligament graft 1602 into the bone holes 1302, 1504 formed in the femur 108 and the tibia 106, a surgeon can first place the opposed ends of the ligament graft 1602 into the conical bone hole 1302 formed in the femur 108 from the lateral (i.e., outer) side of the hole 1302. As the sutures 1608, 1610 or opposed ends of the ligament graft 1602 emerge from the medial (i.e., inner) end of the conical bone hole 1302, graspers can be used to introduce the ligament graft 1602 into the bone hole 1504 formed in the tibia 106 from a superior (i.e., upper) surface thereof.

Figure 17:
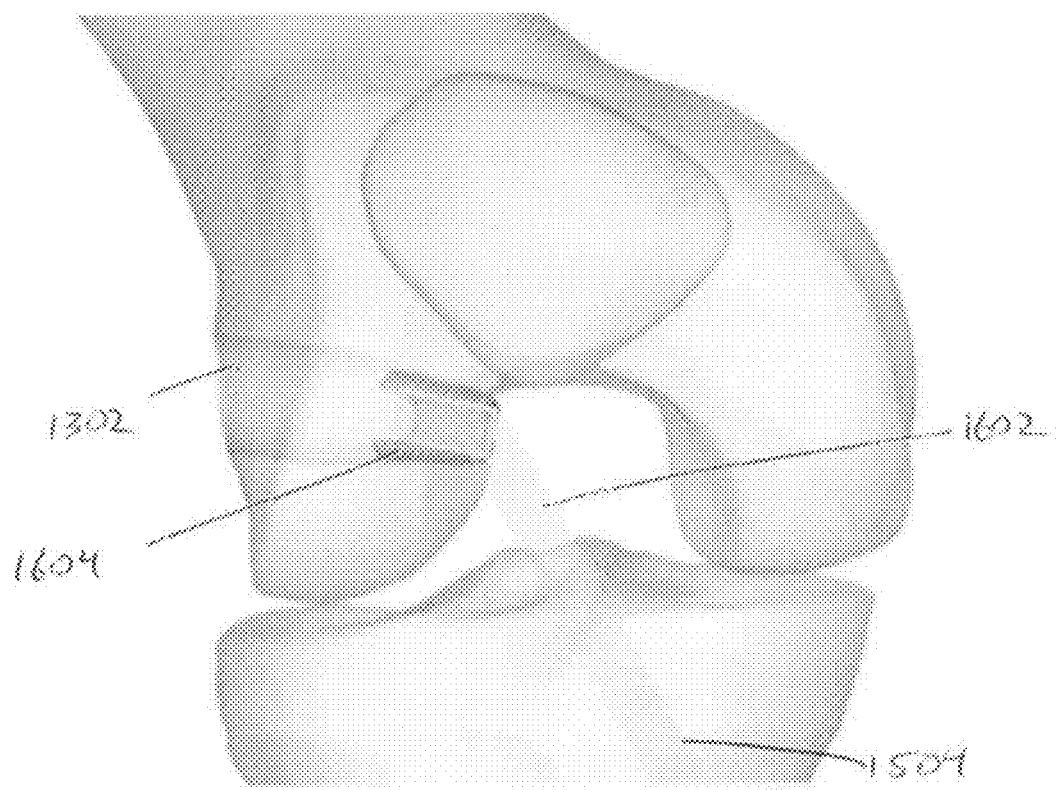
FIG. 17 is an illustration the ligament graft and implant of FIG. 16 form fitted in the femur of FIG. 13.

At this point, a surgeon can rotate the implant 1604 and the ligament graft 1602 as necessary to achieve the most effective biomechanical orientation of the graft 1602. This can be done by manipulating the implant 1604 via the suture passed through the bore formed in the implant 1604 and extending out of the lateral side of the bone hole 1302. This same suture can be used to remove the graft 1602 if necessary. When the desired orientation has been achieved, the opposed ends of the ligament graft 1602 can be pulled tight toward the inferior medial end of the bone hole 1504 formed in the tibia 106, which will cause the implant 1604 to be pulled into a secure friction form fit with the conical bone hole 1302 formed in the femur 108, as shown in FIG. 17. The implant 1604 and the ligament graft 1602 can thus be placed using the sutures 1608, 1610 without inserting any instrument into the bone conical bone hole 1302 formed in the femur 108, thereby eliminating a need to create fixation with any instrument. Instead, as discussed herein, fixation can be achieved via the friction form fit.

Figure 18:
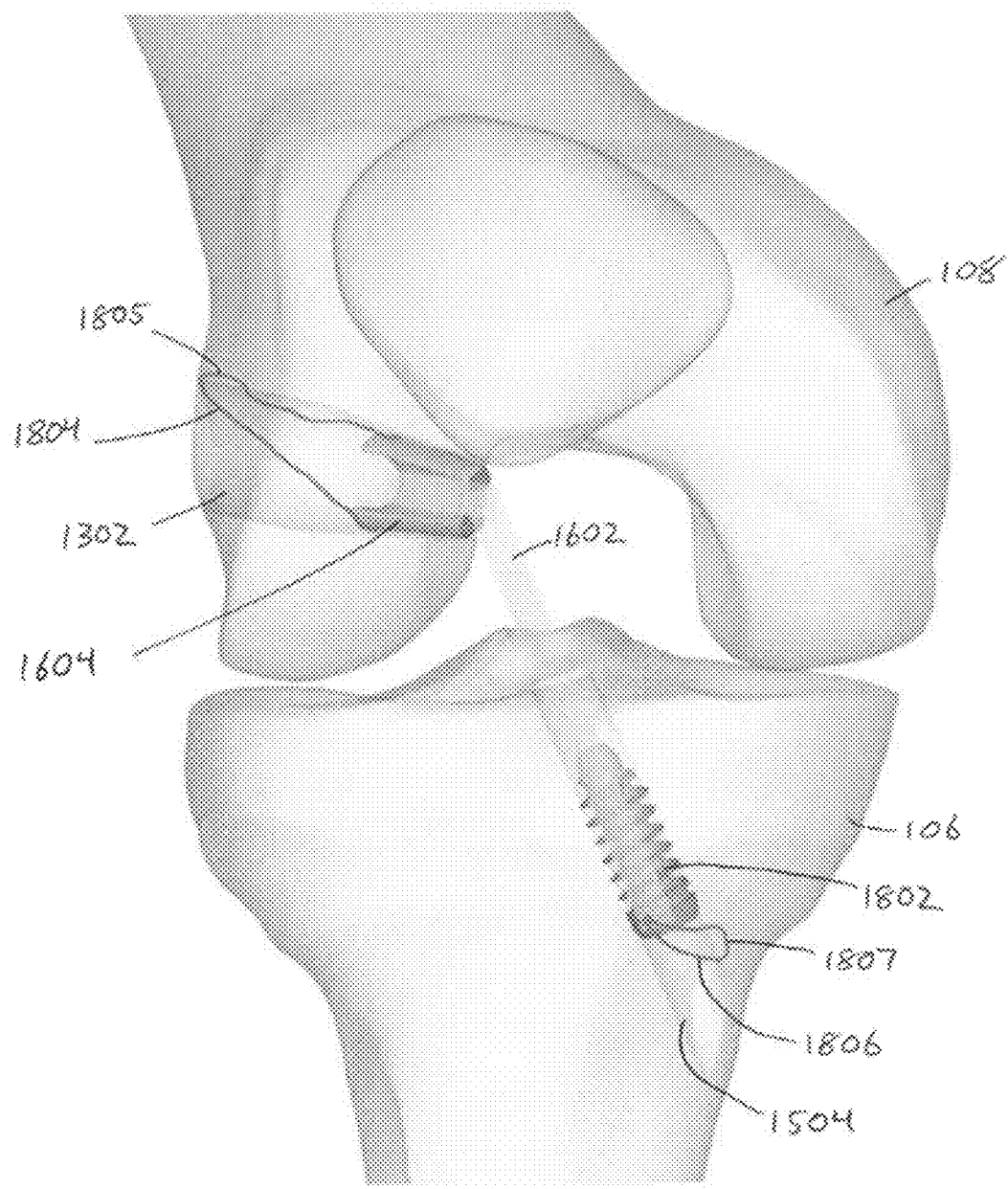
FIG. 18 is an illustration of the ligament graft and implant of FIG. 16 secured in the femur of FIG. 13 and the tibia of FIG. 15.

To complete the procedure, an interference screw 1802 can be introduced into the bone hole 1504 formed in the tibia 106 in order to secure the opposed ends of the ligament graft 1602, as shown in FIG. 18. The interference screw 1802, in combination with the friction form fit of the implant 1604 in the conical bone hole 1302 of the femur 108, will secure the ligament graft 1602 in place, allowing it to function as a replacement anterior cruciate ligament.

If additional reinforcement is desired, a surgeon can also utilize sutures to create trans-osseous bridges between the implant 1604 and the femur 108 or the interference screw 1802 and the tibia 106. As shown in FIG. 18, for example, a suture 1804 passed through the bore of the implant 1604 can also be passed through a secondary bone hole 1805 formed in the femur 108. The suture 1804 can be drawn tight and tied off such that the suture 1804 can provide additional securement for the implant 1604. A similar procedure can be conducted with a suture 1806 coupled to the interference screw 1802 and passed through a secondary bone hole 1807.

All papers and publications cited herein are hereby incorporated by reference in their entirety. One skilled in the art will appreciate further features and advantages of the invention based on the above-described embodiments. Accordingly, the invention is not to be limited by what has been particularly shown and described, except as indicated by the appended claims.

What is claimed is:

1. An implant for securing a ligament graft, comprising:
a body having a conical outer profile extending along a longitudinal axis thereof between a proximal end of the body and a tapered distal end of the body, wherein the body includes:
a first set of opposed slots formed in an outer surface thereof that extend along the longitudinal axis and a transverse slot formed in the proximal end that extends between the first set of opposed slots;
a bore formed through the body that is transverse to the longitudinal axis and angularly offset from the first set of opposed slots; and
a second set of opposed slots formed in the outer surface thereof that extend proximally from the bore and terminate at the proximal end of the body.

2. The implant of claim 1, wherein the bore has first and second bore holes in the outer surface of the body, and the second set of opposed slots have terminal distal ends at the first and second bore holes.

3. The implant of claim 2, wherein the first and second bore holes are at a terminal distal end of the set second of opposed slots.

4. The implant of claim 2, wherein the first and second bore holes are inset in the body such that when a suture extends through the bore and is seated in the second set of opposed slots the suture does not protrude radially outward from the outer surface of the body.

5. The implant of claim 1, wherein the distal end of the body is substantially flat.

6. The implant of claim 1, wherein outer edges of the body are radiused.

7. The implant of claim 1, wherein the body is formed from tricalcium phosphate.

8. The implant of claim 1, wherein the body is formed from a polymer.

9. The implant of claim 1, wherein the distal end of the body has an outer perimeter and is a continuous surface within an entire surface area defined within the perimeter.

10. The implant of claim 9, wherein the continuous surface is substantially flat.

11. A system for positioning and securing a ligament graft, comprising:
 an implant having a conical outer profile and a groove formed therein that extends along a longitudinal axis of the implant and around a proximal end thereof, the groove being configured to seat a middle portion of a ligament graft such that opposed ends of the ligament graft extend beyond a distal end of the implant; and
 a reamer with a distal-most portion having a conical outer profile that matches the implant, the reamer being configured to form a conical hole in bone that is configured to accept the implant.

12. The system of claim 11, wherein the implant further includes a bore formed through the implant that is transverse to the longitudinal axis and angularly offset from the groove.

13. The system of claim 12, wherein the implant further includes opposed slots formed in an outer surface thereof that extend between first and second bore holes of the bore and the proximal end of the implant.

14. The system of claim 12, further comprising a suture length passed through the bore such that opposed ends of the suture length extend beyond the proximal end of the implant.

15. The system of claim 11, wherein the reamer includes at least one depth marking configured to indicate a size of the conical hole formed.

16. The system of claim 11, wherein the reamer includes a handle at a proximal end thereof configured to manually actuate the reamer.

17. The system of claim 11, wherein the distal end of the implant is substantially flat, and a distal end of the reamer is substantially flat.

* * * * *